(12) United States Patent
Adachi et al.

(10) Patent No.: US 8,461,112 B2
(45) Date of Patent: Jun. 11, 2013

(54) HGF PREPARATION

(75) Inventors: Kiichi Adachi, Osaka (JP); Keigo Hanada, Osaka (JP)

(73) Assignee: Kringle Pharma Inc., Osaka (JP)

( * ) Notice: Subject to any disclaimer, the term of this patent is extended or adjusted under 35 U.S.C. 154(b) by 307 days.

(21) Appl. No.: 12/432,651

(22) Filed: Apr. 29, 2009

(65) Prior Publication Data

US 2009/0233863 A1    Sep. 17, 2009

Related U.S. Application Data

(63) Continuation of application No. PCT/JP2008/052979, filed on Feb. 21, 2008, and a continuation-in-part of application No. PCT/JP2007/053316, filed on Feb. 22, 2007.

(51) Int. Cl.
*A61K 38/18* (2006.01)

(52) U.S. Cl.
USPC .......................................................... 514/9.5

(58) Field of Classification Search
None
See application file for complete search history.

(56) References Cited

U.S. PATENT DOCUMENTS

| 6,699,837 | B2 | 3/2004 | Nakamura |
| 6,869,609 | B1 | 3/2005 | Yamazaki et al. |
| 6,887,477 | B1 | 5/2005 | Nagano et al. |
| 7,173,008 | B2 * | 2/2007 | Tanaka et al. ................... 514/7.6 |
| 7,432,044 | B2 * | 10/2008 | Kirchhofer et al. ................ 435/4 |
| 2001/0051604 | A1 | 12/2001 | Tanaka et al. |
| 2007/0161081 | A1 * | 7/2007 | Jin et al. ........................ 435/69.1 |
| 2008/0039380 | A1 * | 2/2008 | Machida et al. ................. 514/12 |

FOREIGN PATENT DOCUMENTS

| CN | 1579544 A | | 2/2005 |
| WO | WO 2005/072768 | * | 8/2005 |

OTHER PUBLICATIONS

Bedu-Addo, Pharmaceutical Technology: Lyophilization 2004, pp. 10-18.*
"Protein, nucleic acid and enzyme" 1992, vol. 37, No. 9, pp. 1517-1523 (Partial Translation).
Sun, et al., "Stabilizing Excipients in the Freeze-dried Protein Formulations and their Protective Mechanisms" Progress in Pharmaceutical Sciences, 2003, pp. 201-205, vol. 27, Nor. 4 (Abstract).

* cited by examiner

*Primary Examiner* — Marianne P Allen

(57) ABSTRACT

The present invention relates to an HGF preparation comprising HGF and purified sucrose. The HGF preparation is characterized by being stable even after a long-term storage.

4 Claims, No Drawings

HGF PREPARATION

CROSS-REFERENCE TO RELATED APPLICATIONS

The present application claims the benefit of priority to and is a continuation of PCT/JP2008/052979, filed on Feb. 21, 2008, and the present application claims the benefit of priority to and is a continuation-in-part of PCT/JP2007/053316, filed Feb. 22, 2007. The aforementioned applications PCT/JP2008/052979 and PCT/JP2007/053316 are hereby expressly incorporated by reference in their entireties.

TECHNICAL FIELD

The present invention relates to an HGF (Hepatic Growth Factor)-containing preparation.

BACKGROUND ART

HGF is a physiologically active peptide discovered by Nakamura et al, having the most potent mitogenic activity against mature hepatocytes (see, for example, Non-patent Document 1), and its mass production has become possible by bioengineering techniques in recent years (see, for example, Non-patent Document 2). This HGF is expected as a therapeutic or preventive agent for not only hepatitis and hepatic cirrhosis but also nephritis, cancers, etc., and is further expected in the application as a suppressant for adverse reactions to anti-cancer agents and as a wound-healing agent.

Among HGF preparations, an aqueous preparation of HGF containing albumin, human serum, gelatin, sorbitol, mannitol, xylitol, etc., as a stabilizer for HGF is disclosed in Patent Document 1. However, the above-mentioned aqueous HGF preparation has a defect that aggregation, turbidity and gelation occur during storage, as well as a problem of low physicochemical stability due to aggregates formation, resulting in reduction of the biological activity of HGF.

In order to solve these problems, a freeze-dried preparation wherein arginine, lysine, histidine, glutamine, proline, glutamic acid, aspartic acid, etc. are contained as a stabilizer for HGF is disclosed in Patent Document 2. Further, in Patent Document 3, a freeze-dried preparation wherein glycine, alanine, sorbitol, mannitol, dextran sulfate, etc., are added as a stabilizer to HGF is disclosed.

Although the above-mentioned freeze-dried preparations can attain stabilization of HGF to some extent, an HGF preparation with a still more sufficient stabilization effect has been demanded.

[Patent Document 1] PCT International Publication WO 90/10651 Pamphlet
[Patent Document 2] PCT International Publication WO 00/72873 Pamphlet
[Patent Document 3] Japanese Patent Application Laid-Open (JP-A) No. 9-25241
[Non-patent Document 1] Biochem. Biophys. Res. Commun., 122, 1450, 1984
[Non-patent Document 2] Nature, 342, 440, 1989.

DISCLOSURE OF THE INVENTION

Problems to be Solved by the Invention

It is an object of the present invention to provide a more stable HGF preparation when stored for a long term as compared with the conventional HGF preparation.

Means for Solving the Problems

The inventors of the invention conducted various studies to achieve the foregoing problems. As a result, they found that a stable HGF preparation was obtained by adding purified sucrose to HGF so that the formation of HGF aggregates was suppressed. Studies based on the above findings were further made to complete the invention.

Namely, the invention relates to:

[1] an HGF preparation comprising HGF and purified sucrose,
[2] the HGF preparation according to the above item [1], wherein the purified sucrose content is 0.01 to 9 parts by weight based on 1 part by weight of HGF,
[3] the HGF preparation according to the above item [1] or [2], further comprising a neutral amino acid,
[4] the HGF preparation according to the above item [3], wherein the neutral amino acid is alanine,
[5] the HGF preparation according to any one of the above items [1] to [4], further comprising a buffer,
[6] the HGF preparation according to the above item [5], wherein the buffer is a citric acid salt,
[7] the HGF preparation according to any one of the above items [1] to [6], further comprising sodium chloride,
[8] the HGF preparation according to the above item [1] or [2], further comprising a neutral amino acid, sodium chloride, a buffer and a surfactant, in addition to HGF and purified sucrose,
[9] the HGF preparation according to the above item [8], wherein the neutral amino acid is alanine, the buffer is a citric acid salt, and the surfactant is a Polysorbate,
[10] the HGF preparation according to any one of the above items [1] to [9], which is a freeze-dried preparation,
[11] a stabilization method of HGF, which comprises suppressing the formation of HGF aggregates by adding purified sucrose to HGF, and
[12] the stabilization method according to the above item [11], wherein the addition amount of purified sucrose is 0.01 to 9 parts by weight based on 1 part by weight of HGF.

Effect of the Invention

The HGF preparation of the invention has a more stable effect even after a long-term storage as compared with the conventional HGF preparations.

BEST MODE FOR CARRYING OUT THE INVENTION

The invention relates to an HGF preparation comprising HGF and purified sucrose.

The active ingredient HGF prepared by various processes can be used in the present invention if it is purified enough to be used as a medicine. Further, HGF used in the invention may be a deletion type of HGF, which lacks five amino acid residues (referred to as dLeHGF).

Various methods are known for preparing HGF. For example, HGF can be obtained by extraction and purification from organs (e.g. liver, spleen, lung, bone marrow, brain, kidney, placenta, etc.), blood cells (e.g. platelets, leukocytes, etc.), plasma, and serum of mammals including rat, cow, horse, sheep, and the like. Also, HGF can be obtained by cultivating primary culture cells or cell lines capable of producing HGF, followed by isolation and purification from the culture (e.g. culture supernatant, cultured cells, etc.). Further, a recombinant HGF can also be obtained according to a gene technology by integrating a gene encoding HGF into an appropriate vector, inserting the vector into a proper host cell to give a transformant, and separating the desired recombinant HGF from the culture of the transformant (see, for example, Nature, 342, 440, 1989). The above-mentioned host cells are not particularly limited, and various host cells conventionally used in gene technologies, such as *Escherichia coli, Bacillus subtilis*, yeasts, filamentous fungi, and plant or animal cells can be used.

More specifically, the method of extracting and purifying HGF from biological tissues comprises, for example, administering carbon tetrachloride to rats intraperitoneally, removing the liver from the rats with hepatitis, grinding it, and purifying HGF by the conventional protein purifying technique, such as gel column chromatography on S-Sepharose or heparin-Sepharose, and HPLC and the like. In addition, by use of a gene recombinant technique, an animal cell (e.g. Chinese hamster ovary (CHO) cells, mouse C127 cells, monkey COS cells, etc.) is transformed by an expression vector, wherein a gene encoding the amino acid sequence of human HGF is inserted into a vector such as bovine papilloma virus DNA, and HGF can be obtained from the culture supernatant of the transformants.

The purified sucrose for use in the present invention is one which is listed in Japanese Pharmacopoeia, Fourteenth Edition, Part II, and it can be used preferably as a stabilizer. The addition amount of the purified sucrose is preferably 0.01 to 9 parts by weight, especially preferably 0.1 to 5 parts by weight, based on 1 part by weight of HGF. The lower limit of the addition amount of the purified sucrose is more preferably 0.5 part by weight based on 1 part by weight of HGF. The upper limit of the addition amount of the purified sucrose is more preferably 4 parts by weight, still more preferably 3 parts by weight, and especially preferably 2 parts by weight, based on 1 part by weight of HGF.

Although the preparation of this invention may take various dosage forms (for example, liquid preparations, solid preparations, capsules, creams, sprays, etc.), an aqueous preparation, a freeze-dried preparation and the like containing generally HGF as an active ingredient and purified sucrose alone or a conventional additive (carrier, etc.) in addition to them are preferable, and in particular, a freeze-dried preparation is preferable.

Regarding the HGF preparations of the invention, an aqueous preparation can be prepared through the formation of an aqueous solution containing HGF and purified sucrose. Also, a freeze-dried preparation of HGF can be prepared by freeze-drying said aqueous solution in a conventional freeze-drying method. The purified sucrose content in the aforementioned aqueous solution is 0.1% or more by weight, preferably 0.5% or more by weight, and is 9% or less by weight, preferably 5% or less by weight, more preferably 4% or less by weight, still more preferably 3% or less by weight, especially preferably 2% or less by weight. The purified sucrose content in the freeze-dried preparation is preferably 10 to 80% by weight and especially preferably 20 to 60% by weight. For example, the freeze-dried preparation can be prepared by dissolving HGF in a suitable solvent (e.g. sterilized water, distilled water for injection, buffer, physiological saline, etc.); adding purified sucrose to the solution to a concentration of preferably 0.1 to 5% by weight and especially preferably 0.5 to 2% by weight; optionally adding stabilizers, buffers, surfactants, sodium chloride, etc., other than purified sucrose; sterilizing the solution through filtration with a filter or the like; filling the solution in a vial or ampoule; and freeze-drying the solution. It is preferable to use a sterilization filter with a pore size of 0.22 μm or less. The sterilization filter includes, for example, DURAPORE (Registered trade mark, manufactured by Nihon Millipore K.K.) and SARTOPORE 2 (Registered trade mark, manufactured by Sartorius AG.). An example of the freeze-drying methods includes, for example, a method comprising three unit operations: a freezing step for chilling and freezing under atmospheric pressure, a primary drying step for sublimating and drying free water not restrained by a solute under reduced pressure, and a secondary drying step for removing adsorbed water or crystal water intrinsic to the solute. The chilling temperature in the freezing step is preferably −60 to −40° C., the temperature in the primary drying step is preferably −50 to 0° C., and the temperature in the secondary drying step is preferably 4 to 40° C. The vacuum pressure is preferably 0.1 to 1.5 Pa, and in particular, preferably 0.5 to 1.2 Pa. After the freeze-drying operation, the pressure in the drying chamber is recovered. The method for the pressure recovery is preferably a method of introducing a sterilized air or an inert gas (e.g. sterile nitrogen gas, sterile helium gas) into the chamber to return the pressure back to about 70 to 100 kPa, preferably about 80 to 95 kPa (primary pressure recovery) and then to the atmospheric pressure (secondary pressure recovery). Capping for vials is preferably carried out after the primary pressure recovery.

Purified sucrose alone may be used as the stabilizer. However, purified sucrose may be preferably used in combination with a conventional stabilizer such as amino acids (e.g. glycine, alanine, arginine, lysine, histidine, etc.), polysaccharides (e.g. heparin, dextran sulfate, etc.), and sugar alcohols (e.g. sorbitol, mannitol, etc.). Among these stabilizers, amino acids are preferable, and in particular, neutral amino acids such as glycine and alanine are preferable among the amino acids. The amount of each of these stabilizers to be added is not limited except for purified sucrose, and when the neutral amino acid such as glycine and alanine is used, its addition amount is preferably 0.01 to 50 parts by weight, and more preferably 0.1 to 20 parts by weight based on 1 part by weight of purified sucrose.

Stability of HGF can be more improved by combination use of purified sucrose with a conventional stabilizer including a neutral amino acid, when compared to the case where purified sucrose alone is used as a stabilizer.

The buffer used in the invention includes, for example, a phosphoric acid buffer, a citric acid buffer, and the like. The buffer has an action of adjusting the pH of an aqueous solution after redissolution of the freeze-dried preparation, and maintaining the solubility of HGF. It is preferable to use a buffer which enables to maintain the pH of the aqueous solution at 4.5 to 6.5 after redissolution of the freeze-dried preparation. A preferable buffer is a citric acid buffer and especially sodium citrate buffer. This citric acid buffer also contributes to the stabilization of HGF in the aqueous solution obtained upon redissolution of the freeze-dried preparation. It is desirable to adjust the concentration of the buffer to be added, within the range of 1 to 100 mM in the aqueous solution immediately before the freeze-drying operation for the production of freeze-dried preparations.

Surfactants used in the invention include, for example, Polysorbate 20, Polysorbate 80, Pluronic F-68, polyethylene glycols, etc., and two or more kinds thereof may be used in combination. An especially preferred surfactant is Polysorbate-based surfactants, including particularly Polysorbate 80. Although HGF is easy to be adsorbed on the surface of the materials of the container made of glass or resins, the adsorption of HGF onto the container after redissolution of the freeze-dried preparation, can be prevented by the addition of such a surfactant. As for the addition amount of the surfactant, the concentration of the aqueous solution just before freeze-drying operation in the production of freeze-dried preparations is preferably 0.001 to 2.0% by weight.

Sodium chloride has an action to maintain the solubility of HGF. That is, for example, in the case of the recombinant HGF used in the Examples, addition of sodium chloride makes it possible to increase the solubility of HGF. Particularly, a remarkable improvement in the solubility of the recombinant HGF is observed at a concentration of 300 mM or more of sodium chloride. Although the addition amount of sodium chloride receives a restriction by an osmotic pressure ratio, an amount showing the osmotic pressure ratio of injectable solutions generally used may be good. It is desirable to use an addition amount of sodium chloride reaching an osmotic pressure ratio of 1 to 3, which is an acceptable osmotic pressure ratio of injections for medical use in humans or animals. Usually, when a freeze-dried preparation is manufactured, the concentration of sodium chloride in an aqueous solution just prior to its freeze-drying operation is preferably in the range of 150 to 1000 mM.

The preparation of the invention may include other additives necessary for formulating preparations, such as solubilizers, antioxidants, soothing agents, isotonic agents, and the like.

The preparation obtained above in accordance with the invention, e.g. a freeze-dried preparation, is dissolved in distilled water for injection so that the concentration of HGF in use is in the range of 0.1 to 40 mg/mL, and the solution can be served as an injectable solution. In addition, an external preparation, such as creams, sprays, etc., containing the freeze-dried preparation may be formulated.

EXAMPLES

The following Examples further illustrate the present invention but are not to be construed to limit the scope thereof. In the Examples of the invention, a five amino acid deletion type of HGF was used as HGF. The area percentage (%) (hereinafter referred to as aggregates content (%)) of the HGF aggregates was determined according to the following equation 1 using measured values which were quantitatively analyzed by high performance liquid chromatography (HPLC).

$$\text{Aggregates content (\%)} = \frac{A_A}{A_M + A_A} \times 100 \quad \text{Equation 1}$$

In the equation, $A_M$ is the peak area of HGF and $A_A$ is the peak area of HGF aggregates.

(Conditions for HPLC)

Column: Gel filtration column (Trade name: Superdex 200 10/300, manufactured by Amersham Biosciences)

Mobility phase: sodium chloride 58.44 g, trisodium citrate dihydrate 2.94 g, and Polysorbate 80 0.1 g are dissolved in water to make up to 1 L, which is served as Solution A. Sodium chloride 58.44 g, citric acid monohydrate 2.10 g, and Polysorbate 80 0.1 g are dissolved in water to make up to 1 L, which is served as Solution B. Solution B is added to Solution A and the pH is adjusted to 6.0. The mixed solution is filtered with a 0.45 μm filter (Trade name: Millicup-HV, pore size: 0.45 μm, manufactured by Millipore Corp.) and degassed prior to its use. The solution is stored at room temperature and used within two weeks.

Column temperature: 25° C.
Flow rate: 0.5 mL/min
Injection amount of sample: 25 μL
Analysis time: 60 minutes Detector: absorption spectrophotometer
Detection wave length: 280 nm
Sample cooler: 5 minutes A molecular weight marker is dissolved in one vial of Gel Filtration Standard (Catalogue Number: 151-1901, manufactured by Bio-Rad Laboratories, Inc.) with water (500 μL), and the solution is filtered through a filtration filter (Trade name: Ultrafree-MC, pore size: 0.45 μm, manufactured by Millipore Corp.) for use in clarification of test solutions in small quantities, stored at 2 to 8° C., and used within 3 months.

The buffer solution for dilution used in the following Examples and Test Examples was prepared in the following manner.

(Preparation of Buffer Solution for Dilution)

Sodium chloride 1.1688 g, trisodium citrate dihydrate 2.94 g and Polysorbate 80 0.3 g were dissolved in ultra pure water to make up to a total volume of 1 L, and the solution was served as Solution A. Sodium chloride 1.1688 g, citric acid monohydrate 2.10 g, and Polysorbate 80 0.3 g were dissolved in ultra pure water (prepared by using an apparatus for ultra pure water production; Trade name: MilliQ Gradient, manufactured by MilliPore Corp.; hereinafter the same) to make up to 1 L, which was served as Solution B. Solution B was added to Solution A and the pH was adjusted to 6.0. The solution was served as a buffer for dilution (1).

Sodium chloride 17.53 g, trisodium citrate dihydrate 2.94 g, and Polysorbate 80 0.1 g were dissolved in ultra pure water to make up to a total volume of 1 L, which was served as Solution C. Sodium chloride 17.53 g, citric acid monohydrate 2.10 g, and Polysorbate 80 0.1 g were dissolved in ultra pure water to make up to a total volume of 1 L, which was served as Solution D. Solution D was added to Solution C, and the pH of the solution was adjusted to 6.0. This solution was served as a buffer for dilution (2).

Example 1

The five amino acids-deleted type of HGF (hereinafter, simply referred to as HGF) was added to a buffer for dilution (1) so that HGF concentration became to be 10 mg/ml, and purified sucrose was then added thereto to a concentration of 0.5% by weight, thereby to obtain solutions with the components as shown in Table 1 below.

TABLE 1

| Component | Concentration |
| --- | --- |
| HGF | 10 mg/ml |
| Trisodium citrate dihydrate | 10 mM |
| Sodium chloride | 300 mM |
| Polysorbate 80 | 0.03% by weight |
| Purified sucrose | 0.5% by weight |

Each (2 mL) of the solutions obtained above was aseptically subdivided into a vial (φ23×43 mm). The vial was semi-capped with a rubber stopper, arrayed on a tray, placed in a freeze-dryer (Triomaster; manufactured by Kyowa Vacuum Engineering Ltd.) and then freeze-dried under the conditions as shown in Table 2 below. The arrow symbol "→" in the table shows that the temperatures was changed.

TABLE 2

|  | Freezing Step | | Primary Drying Step Temperature (° C.) | | Secondary Drying Step | |
|---|---|---|---|---|---|---|
|  | 10 → −50 | −50 | −50 → −20 | −20 | −20 → 20 | 20 |
| Degree of Vacuum (Pa) | — | — | 1 | 1 | 1 | 1 |
| Time (hr) | 6 | 5 | 8 | 33.5 | 8 | 11 |

After freeze-drying operation, a sterile nitrogen gas was introduced into the chamber of Triomaster to recover the pressure (chamber pressure: 88.0 kPa; primary pressure recovery), and each of the vials was fully capped with a rubber stopper. After that, the pressure in the chamber of Triomaster was recovered to the atmospheric pressure with a sterile nitrogen gas (secondary pressure recovery), and vials were taken out, immediately followed by capping with a stopper. In this manner, freeze-dried preparations of HGF according to the invention were obtained.

The purified sucrose content in the freeze-dried preparation is 0.5 part by weight based on 1 part by weight of HGF, and is 26.3% by weight to the freeze-dried preparation.

Example 2

A freeze-dried preparation of HGF was obtained in a manner similar to Example 1, except that the concentration of purified sucrose to be added was 1.0% by weight.

The purified sucrose content in the freeze-dried preparation of HGF of the invention is 1 part by weight based on 1 part by weight of HGF and is 41.7% by weight to the freeze-dried preparation of HGF.

Example 3

A freeze-dried preparation of HGF was obtained in a manner similar to Example 1, except that the concentration of purified sucrose to be added was 2.0% by weight.

The purified sucrose content in the freeze-dried preparation of HGF is 2 parts by weight based on 1 part by weight of HGF and is 58.8% by weight to the freeze-dried preparation of HGF.

Example 4

A freeze-dried preparation of HGF was obtained in a manner similar to Example 1, except that purified sucrose and alanine were added at a concentration of 1.0% by weight and 5 mg/mL, respectively.

The purified sucrose content in the freeze-dried preparation of HGF is 1 part by weight based on 1 part by weight of HGF and is 34.5% by weight to the freeze-dried preparation of HGF.

Comparative Example 1

A freeze-dried preparation of HGF was obtained in a manner similar to Example 1, except that alanine was added as an additive at a concentration of 20 mg/mL in place of purified sucrose.

Comparative Example 2

A freeze-dried preparation of HGF was obtained in a manner similar to Example 1, except that purified sucrose was not added (hereinafter referred to as a basic formulation).

Test Example 1

The freeze-dried preparations described in the above Examples and Comparative Examples were stored at 50° C. and sampled after one week. Each of the samples was diluted with a buffer for dilution (2) so that the concentration of the protein was 5 mg/mL. Each sample was quantified using HPLC, and the content (%) of HGF aggregates was calculated according to the above equation 1. The results are shown in Table 3 below.

TABLE 3

|  | Additive (Concentration) | | Aggregates content (%) | | |
|---|---|---|---|---|---|
|  |  |  |  | At the |  |
| Example No. | Purified sucrose | Alanine | Before freeze-drying | beginning of storage (Initial) | 50° C., 1 week |
| Example 1 | +(0.5% by weight) | — | 0.47 | 0.61 | 1.90 |
| Example 2 | +(1.0% by weight) | — | 0.48 | 0.58 | 1.29 |
| Example 3 | +(2.0% by weight) | — | 0.48 | 0.56 | 0.92 |
| Example 4 | +(1.0% by weight) | +(5 mg/mL) | 0.44 | 0.56 | 0.90 |
| Comparative Example 1 | — | +(20 mg/mL) | 0.50 | 0.63 | 2.32 |
| Comparative Example 2 | — | — | 0.55 | 0.84 | 6.12 |

As apparent from Table 3, in an HGF preparation of the basic formulation+purified sucrose and an HGF preparation of the basic formulation+purified sucrose+alanine according to the present invention, the content of HGF aggregates was suppressed more significantly, when compared with an HGF preparation of the basic formulation or the basic formulation+alanine.

Test Example 2

HGF was added to a buffer solution for dilution (20 mM citric acid buffer solution, 1M sodium chloride, Polysorbate 80 0.01% by weight) to a concentration of 10 mg/L, and sample solutions 1 to 5 (50 μL each) were prepared in such a manner that purified sucrose was added to a concentration of 0% by weight, 1% by weight, 5% by weight, 10% by weight or 20% by weight. Each sample solution was frozen for about 24 hours until measurement. Each of the frozen sample solutions was redissolved, and molecular weight (about 84 kDa) distribution of HGF was then measured by the dynamic light scattering (DLS) method. Dyna-Pro (manufactured by Protein-Solution Co.) for exclusive use of protein solutions was used as the measurement device. The measurement temperature was set to 4° C. A buffer (50 μL each) for dilution not containing HGF was used as the background. The degree of polydispersity (Pd %) of HGF molecular weights in each of the sample solutions is shown in Table 4.

TABLE 4

|  | HGF (mg/mL) | Purified sucrose (% by weight) | Pd % |
|---|---|---|---|
| Sample solution 1 | 10 | 0 | 22.8 |
| Sample solution 2 | 10 | 1 | 21.7 |
| Sample solution 3 | 10 | 5 | 13.6 |

TABLE 4-continued

|  | HGF (mg/mL) | Purified sucrose (% by weight) | Pd % |
|---|---|---|---|
| Sample solution 4 | 10 | 10 | 32.3 |
| Sample solution 5 | 10 | 20 | 28.5 |

As apparent from Table 4, in the sample solutions 2 and 3 wherein purified sucrose was added to a concentration of 1% by weight and 5% by weight, respectively, Pd % value was very small and the molecular weight distribution of HGF was found to be a single distribution (monomodal distribution). In the sample solutions 1, 4, and 5, the peak of the HGF molecular weight was broad, suggesting that HGFs having different molecular weights were contained in such sample solutions. Moreover, in the sample solutions 4 and 5, another peak appeared in the high molecular side, and in the sample solution 5, a peak showing that a large amount of lower molecular weight substances were contained therein was observed.

INDUSTRIAL APPLICABILITY

HGF preparations useful as drugs and excellent in storability can be provided in accordance with the invention.

The invention claimed is:

1. A composition comprising Hepatocyte Growth Factor (HGF), sucrose, alanine, sodium chloride, a citric acid salt and a Polysorbate, wherein said composition is freeze-dried.

2. The composition according to claim 1, wherein the sucrose in said composition is 0.01 to 9 parts by weight for 1 part of HGF.

3. A method of making the composition of claim 1 comprising:
   preparing an HGF solution wherein the solution comprises a citric acid buffer, sodium chloride, Polysorbate, sucrose and alanine; and
   freeze-drying the HGF solution containing citric acid buffer, sodium chloride, Polysorbate, sucrose, and alanine.

4. A method for preparing an injectable solution, comprising dissolving the composition of claim 1 in distilled water for injection to obtain the injectable solution.

* * * * *